United States Patent
Hardy et al.

(10) Patent No.: US 6,913,733 B2
(45) Date of Patent: Jul. 5, 2005

(54) APPARATUS AND METHOD FOR DEODORIZING AND/OR FRESHENING AIR

(75) Inventors: Charles Michael Hardy, Norwood, OH (US); Kevin George Goodall, Cincinnati, OH (US); Jeffrey Donald Painter, Loveland, OH (US); Frank Andrej Kvietok, Cincinnati, OH (US); Eric Richard Bartsch, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 113 days.

(21) Appl. No.: 09/972,098

(22) Filed: Oct. 5, 2001

(65) Prior Publication Data

US 2002/0090317 A1 Jul. 11, 2002

Related U.S. Application Data

(63) Continuation-in-part of application No. 09/775,999, filed on Feb. 2, 2001.

(51) Int. Cl.⁷ .............................................. A61L 9/012
(52) U.S. Cl. ...................... 422/124; 422/5; 424/76.21
(58) Field of Search ................... 422/124, 5; 424/76.21

(56) References Cited

U.S. PATENT DOCUMENTS

| | | | |
|---|---|---|---|
| 4,995,556 A | | 2/1991 | Arnold, III |
| 5,234,162 A | * | 8/1993 | Sullivan ..................... 239/56 |
| 5,288,306 A | | 2/1994 | Aibe et al. |
| 5,342,584 A | * | 8/1994 | Fritz et al. .................. 422/124 |
| 5,403,548 A | | 4/1995 | Aibe et al. |
| 5,772,959 A | | 6/1998 | Bermas |
| 6,495,097 B1 | * | 12/2002 | Streit et al. ..................... 422/5 |
| 2002/0106303 A1 | | 8/2002 | Stiros et al. |
| 2002/0178706 A1 | | 12/2002 | Kvietok et al. |
| 2003/0010206 A1 | | 1/2003 | Painter et al. |
| 2003/0019362 A1 | | 1/2003 | Sitros et al. |

FOREIGN PATENT DOCUMENTS

| | | |
|---|---|---|
| DE | 30 02 409 A1 | 7/1981 |
| DE | 298 01 969 U1 | 6/1998 |
| WO | WO 95/15187 | 6/1995 |
| WO | WO 00/33940 | 6/2000 |
| WO | WO 01/56620 A1 | 8/2001 |
| WO | WO 01/56622 A1 | 8/2001 |
| WO | WO 01/56623 A1 | 8/2001 |
| WO | WO 01/62310 A1 | 8/2001 |

* cited by examiner

*Primary Examiner*—Hoa Van Le
(74) *Attorney, Agent, or Firm*—Brent M. Peebles; Jeffrey V. Bamber (57) ABSTRACT

Apparatus and methods for deodorizing and/or freshening the air are disclosed. In one non-limiting embodiment, the apparatus includes one or more passive members and an air moving member. The passive member can be detachable from the air moving member and used separately as a passive filter member, if it contains a deodorizing substance, or as a passive emitting member, if it contains a substance to be emitted into the air. Numerous combinations of passive filter members and passive emitting members can be used with the air moving member, or as stand-alone members in the described methods. In other non-limiting embodiments, devices can be provided that both deodorize and emit substances into the air. Kits are also provided. The substances to be emitted may be arranged in various ways to improve the amount of exposed surface area of the substance to be emitted. Intensity controlling mechanisms are also provided.

4 Claims, 7 Drawing Sheets

APPARATUS AND METHOD FOR DEODORIZING AND/OR FRESHENING AIR

CROSS REFERENCES TO RELATED APPLICATIONS

This application is a continuation-in-part of U.S. patent application Ser. No. 09/775,999 filed Feb. 2, 2001. This application also claims the benefit of the filing date of the following PCT applications: US/00/02907, US/00/03011, US/00/03010, all filed Feb. 2, 2000; US001/05403, filed Mar. 2, 2000; and, US/0013531, filed May 18, 2000.

FIELD OF THE INVENTION

The present invention relates to an apparatus and method for deodorizing and/or freshening air.

BACKGROUND OF THE INVENTION

Oftentimes, it is desirable to remove malodors from the air. In some situations, it is desirable to emit substances into the air.

One situation in which it is desirable to remove malodors from the air is in connection with storing and preserving food in closed compartments and refrigerators. It is a well know problem that many food items tend to release malodors into the air that are then captured in the limited air space in the refrigerator. Not only are these malodors unpleasant and offensive to the user of the refrigerator, they can have a negative impact on the quality of the other foods in the refrigerator. For example, it is known that some foods emit strong odors (e.g., fish, onions) and that these odors can transfer to other foods, including ice, and hurt the taste and freshness of those foods. Other situations in which it is desirable to remove malodors are in connection with pet litter boxes, under sinks where "musty air" can build up, or in closed rooms and cupboards. Again, these odors can be offensive and unpleasant to those in the vicinity.

In other situations, it is desirable to emit a substance into the air including, for example, but not limited to insecticides, and fragrances. A number of articles and devices exist for emitting a fragrance into the atmosphere. However, these are often linked to a wall socket; or have poor diffusivity in a room because they have no air flow; or are less portable; or, in the case of candles, are unsafe if left unattended. In addition, the size of areas to be fragranced can vary, for example, from living or family rooms, to cupboards or closets, or even cars. Also, in many of these devices, the amount of scent emitted cannot be varied or controlled—which can be important depending on the sensitivity of the user and the volume of room to be fragranced. Lastly, it is possible that at certain times, malodor removal will be more important or desired, whereas at other times air fragrancing may be desired.

There exist in the art devices for deodorizing confined spaces such as those disclosed for example in U.S. Pat. No. 5,403,548 and in U.S. Pat. No. 5,772,959. However, some of these devices fail to be capable of deodorizing complexly structured confined spaces that comprise portions that are not normally reached by air convection. These portions include, for example, drawers for fresh fruits and vegetables in a refrigerator. Malodors may be trapped and hence may not be reached by deodorizing devices placed in the main compartment. There also exist in the art devices to emit substances, like a fragrance, for example a device known as the Norelco Aromatherapy System AT 100. Air fragrance devices also may not be able to reach similar confined spaces via normal air convection, and/or may not be portable to allow placement in the areas where safe air fragrancing is desired.

Thus, a need exists for devices and methods for deodorizing and/or freshening the air when desired that are not subject to the drawbacks of some prior art devices and methods. A need exists for a device capable of emitting scents that is safe, and does not present an undue hazard like lit scent-emitting candles. A need exists for devices capable of emitting scents or other substances into the air which do not need to be plugged into an electrical outlet and are portable. In addition, there is a need to provide a device that is capable of emitting scents to confined spaces as well as to larger spaces. A need further exists for a scent-emitting device in which the user is capable of controlling the intensity of the scent emitted therefrom. A need also exists for a scent-emitting device in which the scent medium can be easily replaced so that the device can be reused.

It is therefore an object of the present invention to provide an apparatus and a method for deodorizing and/or freshening air.

SUMMARY OF THE INVENTION

The present invention relates to an apparatus and method for deodorizing and/or freshening air. In one non-limiting embodiment, the apparatus includes one or more passive members and an air moving member. The passive member can be detachable from the air moving member and used separately as a passive filter member, if it contains a deodorizing substance, or as a passive emitting member, if it contains a substance to be emitted into the air. Numerous combinations of passive filter members and passive emitting members can be used with the air moving member, or as stand-alone members in the described methods. In other non-limiting embodiments, devices can be provided that both deodorize and emit substances into the air. Kits are also provided. The substances to be emitted may be arranged in various ways to improve the amount of exposed surface area of the substance to be emitted. Intensity controlling mechanisms are also provided.

DETAILED DESCRIPTION OF THE INVENTION

The present invention relates an apparatus (or "device") and method for deodorizing and/or freshening air. The apparatus and method for deodorizing air can be suitable for use in various confined spaces, including, but not limited to, refrigerators, closets, clothes dressers, and the like. When the device is used for emitting substances, it is possible to effectively use the device in even larger spaces, such as in a room, or closet. The apparatus and method of the present invention are, however, by no means limited to such uses. For example, it also possible for the device, or a portion thereof, to be used on its own for scenting relatively small spaces like the inside of an automobile. The apparatus may also be provided with one or more components that can be used independently to deodorize and/or freshen the air in other locations.

The apparatus of the present invention can be provided in any suitable configuration. In one non-limiting embodiment, an apparatus useful in the present invention comprises a passive member and an air moving member (or "forced air member"). When the apparatus is used for deodorizing the air, the passive member may be referred to as a "passive filter member". When the device is used for emitting substances, the passive member may be referred to as a "passive emitting member". The apparatus of the present invention preferably comprises at least one passive member which can be used with an air moving member and which can be detachable from an air moving member and used separately. This greatly enhances the flexibility of the use of the apparatus of the present invention. The passive members may be filter members, emitting members, or combinations thereof. In such embodiments, the passive members used in the apparatus can have any size and shape as long as they can be used with the air moving member. They can also be of the same shape and/or of the same size.

The term "passive filter member" as used herein refers to those filter members which only rely on unassisted air convection and diffusion to bring malodors within reach of the filter media in the member. The term "passive emitting member" as used herein, refers to emitting members that rely only on diffusion to emit substances into the air.

The term "forced air filter member", as used herein, refers to those filter members which are associated with a forced air moving member which draws air into the device past or through a filter member containing a filter media and increases air flow past or through the filter media above that which is achieved through normal air convection in the space in which the forced air filter member is located. The term "forced air emitting member", as used herein, refers to those emitting members which are associated with a forced air moving member which draws air into the device past or through an emitting member containing a substance to be emitted and increases air flow past or through the substance to be emitted above that which is achieved through normal air convection in the space in which the forced air emitting member is located.

Figure 1:
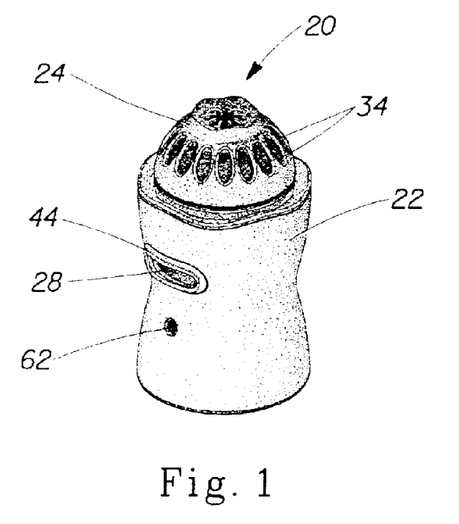
FIG. 1 is a perspective view of one embodiment of the apparatus of the present invention with a cartridge member in place thereon.
Figure 2:
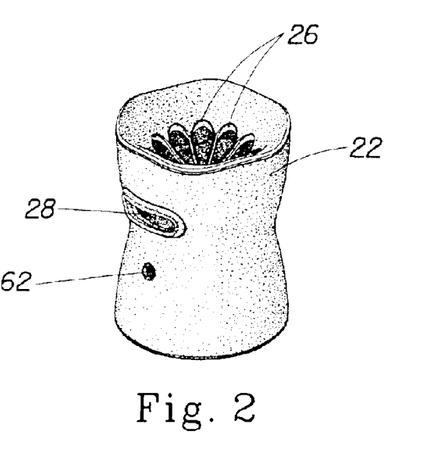
FIG. 2 is a perspective view of the apparatus shown in FIG. 1 with the cartridge removed.

One non-limiting embodiment of the apparatus of the present invention in the form of an air deodorizing device (or simply "the device") 20 is shown in FIG. 1. The apparatus 20 comprises an air moving member 22 and one or more passive filter members, such as passive filter member (or "filter member") 24. The filter member 24 is associated with the air moving member 22. That is, the filter member 24 is used together with the air moving member 22. The filter member 24 is preferably in contact with the air moving member 22, and may either be temporarily attached thereto, or held in contact therewith. In the embodiment shown, the air moving member 22 serves as a base for the filter member 24. The air moving member 22 as shown in FIG. 2, has an air flow path from one or more air inlets 26 to one or more air outlets 28. (There may, for example, be another air outlet 28 on the opposite side of the air moving member from the air outlet 28 shown in FIGS. 1 and 2.) The filter member in this embodiment comprises a cartridge member (or simply "cartridge") 24 and is arranged with the filter element in interaction with the air flowing along the air flow path. In this embodiment, the cartridge member 24 housing the filter element is detachable from the air moving member 22.

The term "detachable", as used herein, refers to members which can be easily removed, in particular where no tools such as screw drivers are needed to remove it from another member such as the air moving member 22. Preferably, no excessive forces are needed for detaching the cartridge member 24. In addition, the cartridge member 24 is preferably directly accessible from outside the air moving member (or other device) 22, and the cartridge member 24 can be removed without opening doors or the like, by holding the air moving member 22 of the present invention in one hand and by removing the cartridge member 24 with the other hand, or by simply lifting the cartridge member 24 off the air moving member 22.

Figure 3:
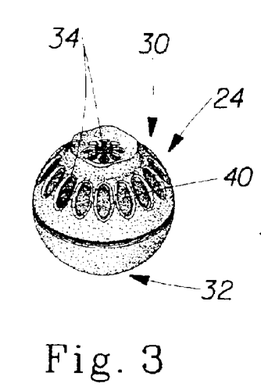
FIG. 3 is a perspective view of the cartridge member used in the embodiment shown in FIG. 1.
Figure 4:
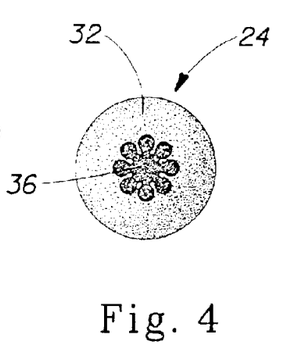
FIG. 4 is a bottom view of the cartridge member.

As shown in FIGS. 3 and 4, the cartridge member 24 has a top portion 30 and a bottom portion 32. The cartridge (in this case, a filter member) 24 may also comprise one or more air inlets 34, one or more air outlets 36, and an air flow path through the filter member from the air inlets to the air outlets. The filter member 24 in this embodiment sits on the top portion of the air moving member 22 so that the outlets 36 on the bottom portion 32 of the filter member 24 are at least partially in alignment with the air inlets 26 on the air moving device 22. In this embodiment, a filter element (or "filter") 40 is disposed in the filter member 24 so that it comes into contact with the air flowing along the air flow path. The filter element 40 is shown in greater detail in FIGS. 6 and 7. The filter element 40 may be arranged as a flow by filter or as a flow through filter. If the filter element 40 is arranged as a flow through filter, the filter element, and the filter medium are preferably sufficiently pervious to air so that air can be conveyed through the filter member. The filter member 24 may comprise a support for the filter medium, for example, in the form of a foam, a nonwoven material or a woven material.

The deodorization of the air in the air deodorizing device of the present invention is enhanced by increasing the air flow through the filter member by means of an air moving member. In one embodiment, to improve the malodor removal performance and to simplify the mechanical construction of the air deodorizing device 20, the filter member 24 and the air moving member 22 are preferably arranged such that substantially all air drawn in by the air moving member 22 is forced to flow through the filter member 24 before it penetrates the air inlet of the air moving member 22. In other words, the air inlet 34 of the cartridge member 24 is preferably in communication with the air inlet 26 of the air moving member 22. In this setup, only one air path connection is needed between the filter member 24 and the air moving member 22 and hence complexity is decreased. Furthermore, withdrawal of the cartridge member 24 is greatly simplified if only one connection has to be disengaged. Any disengageable air flow connection may of course comprise sealing members to improve air flow performance. Any such connection may further comprise mechanical engaging members to stabilize the connection.

The component portions of the embodiment of the apparatus 20 shown in FIG. 1 will now be examined in greater detail.

Figure 5:
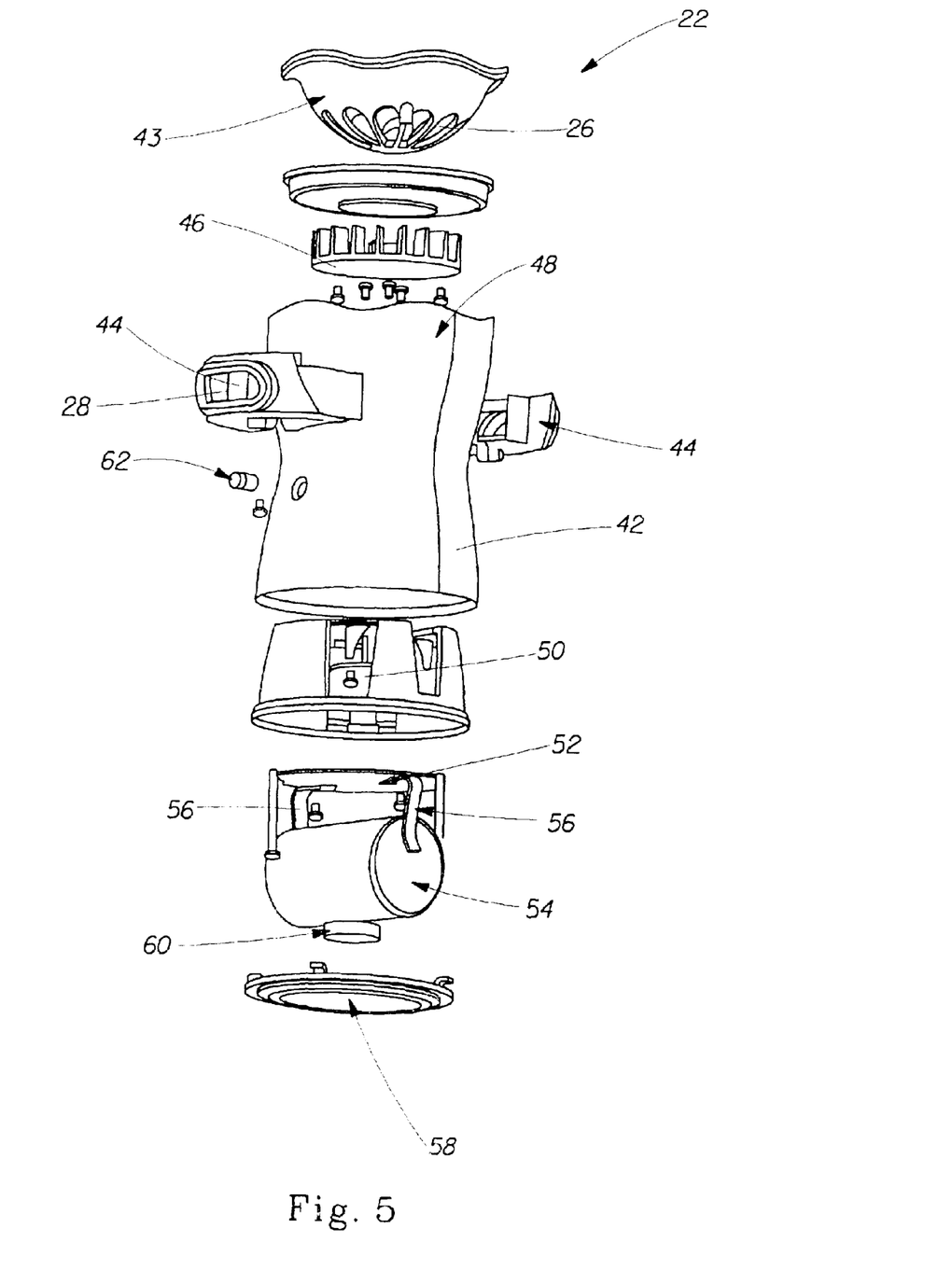
FIG. 5 is an exploded perspective view of the embodiment of the apparatus shown in FIGS. 1 and 2.

FIG. 5 is an exploded view of the air moving member shown 22 in FIGS. 1 and 2. The air moving member 22 comprises a main housing 42 that is sized to contain all of the elements described below. An air inlet member 43 is joined to the main housing 42 to form the top of the air moving member 22. In this embodiment, two air outlet fixtures 44 are installed in the sides of the main housing 24 to form air outlets 28. The filter member 24 will be placed on top of the air inlet member 43 so that air is drawn through the filter member 24 via a suction force. The air can be drawn by a wide variety of suitable air moving members such as, for example, fans and blowers. One suitable air moving member to deliver this suction force is a centrifugal fan 46. The centrifugal fan 46 is contained in a small chamber 48 which helps to maximize the air flow, allowing air to be drawn in near the center of the impeller and expelled perpendicular to the entry direction and through the air outlets 28 of the air moving member 22. The air outlet fixtures 44 are preferably positioned in the main housing 42 such that the rotation of the fan 46 is visible through these outlets. This allows a means of confirming that the fan 46 is operating. Preferably, the air moving member 22 moves at least about 100 mL of air per second through the air inlets 26 into the device, more preferably at least about 200 mL/s most preferably at least about 300 mL/s. A suitable member for driving the fan 46 is a small motor 50, for example a DC motor available from Mabuchi Motor Co., LTD., Japan, under the designation of RF-330TK.

The motor 50 is controlled by a circuit board 52. The air moving members 22 of the present invention are preferably electrically powered. Many electrical power sources can be used, including domestic AC electrical power or power from a static power supply. Alternatively, and preferably, electrical power may be supplied by means of a battery, preferably a dry alkaline cell battery, or a rechargeable battery. In this example, power for the motor is supplied by means of a battery 54, preferably a 1.5 V dry alkaline cell battery, or a rechargeable battery, which is connected to the circuit board by two battery contacts 56. The battery is held into the device by a battery door 58 onto which is adhered a small piece of foam 60 which helps to maintain a tight fit of the battery into the device. The circuit board 52 also contains circuitry controlling a light emitting diode (LED) 62 which is described in greater detail below.

In this example of the device of the present invention, the battery, fan, motor, and circuitry are designed to require a very low power draw, enabling the device 20 to run continuously for a long period of time. Preferably, this embodiment of the device 20 continuously draws less than 20 mA, more preferably less than 10 mA, and most preferably less than 8 mA. To avoid the need for frequent battery replacement, the replaceable power supply of this embodiment preferably is designed to last at least one month, more preferably at least two months, yet more preferably at least three months, most preferably at least four months.

To facilitate ease of use of the device, an indicator is preferred to announce the approaching need to replace the battery. An indicator could be audible, such as a buzzer or whistle; or visual such as a blinking light or raised flag for example. In this example, the indicator is a blinking light emitting diode (LED) 62 which blinks a few dozen times per minute when the voltage of the replaceable power unit falls below about 0.9 V. The LED of this example operates at 3.0 V, much higher than the voltage supplied by the replaceable battery. To enable the operation of this LED, a permanent 3.0 V lithium cell is mounted to the circuit board to power this circuit. The lithium cell is expected to last the lifetime of the device, approximately five years.

FIG. 3 is a perspective view showing one non-limiting example of a filter member 24. This example of a filter member 24 is in the form of a cartridge. The cartridge enables the filter medium to be conveniently handled without the filter medium from spilling out and/or coming into contact with articles in the spaces within which the filter member is placed. The filter member 24 of the present invention comprises one or more air inlets 34, one or more air outlets 36, and air flow path through the filter member 24 from the air inlet 34 to the air outlet 36.

The filter member 24 contains a filter element or filter 40 (shown in greater detail in FIGS. 6 and 7) containing a filter medium. The filter element 40 can be in any suitable configuration, including, but not limited to, disc-shaped, oval, parallelepiped-shaped, rectangular, cube-shaped, cuboid-shaped, cylindrical-shaped, pyramid-shaped, spherical-shaped, irregularly-shaped, or other configuration. In the embodiment shown in the drawings, the filter element 40 can be in the general shape of a sphere, and more particularly is in the shape of several disks of various diameters and thicknesses such that when the disks are placed atop one another they approach the shape of a sphere or a portion thereof, or a cylinder.

The filter medium is disposed in the filter member 24 so that the air flowing along the air flow path is brought into contact therewith. The filter element 40 may comprise a support for the filter medium, for example, in the form of a honeycomb structure, a foam, a nonwoven web or a woven web, or an open-pore reticulate structure, such as a foam or a mesh.

Deodorization of the air to remove malodors by the device of the present invention may be achieved by a filter medium that may neutralize the odors, absorb the malodor molecules, and/or adsorb the molecules constituting a malodor onto a surface of a filter medium. The term "adsorption" is well defined in the art and refers to the adherence of molecules to surfaces which effectively reduces the mobility of these molecules to the two dimensions of the surface. Those molecules remaining in the air will then diffuse so that further molecules come into contact with the surface and subsequently will be adsorbed. Consequently, most of the malodor molecules will travel into the proximity of one of the surfaces at some point in time so that finally most of the malodor will be removed from the air.

The filter member(s) 24 of the present invention may comprise any suitable filter medium or odor removing substance including, but not limited to activated carbon, sodium bicarbonate (i.e., baking soda), cyclodextrin, zeolites, alumina, silicates, carbonates, ozone, acid-treated media, base-treated media, metals (such as silver and platinum), doped media, any other known odor removing substance, and combinations thereof. Activated carbon is known to be a very effective filter medium for adsorption of odors due to its high specific surface area. The filter member 24 of the present invention may further comprise agents supported on the filter element 40 to specifically attack certain malodors such as those comprising S atoms or N atoms. Additionally, or alternatively, the filter member 24 may comprise a filter medium capable of removing ethylene from the air, such as a filter medium comprising potassium permanganate.

If activated carbon is used, the filter member(s) of the present invention preferably comprises at least about 2 grams, more preferably at least about 5 grams, and most preferably at least about 10 grams of activated carbon. Preferably, the filter member of the present invention comprises less than about 100 grams, more preferably less than about 50 grams, yet more preferably less than about 40 grams, and most preferably less than about 30 grams of activated carbon. A wide variety of activated carbon based filter media is known in the art. Suitable forms of supported activated carbon are the reticulated polyurethane foam products which are commercially available from Helsa-Werke, Helmut Sandler GmbH & Co. KG, Germany, under the designations Helsa-tech 8126, 8139, 5600, and 5615.

The filter medium can be arranged in any suitable manner to form the filter element 40. Several non-limiting examples are as follows. The filter medium may be provided in a loose form (such as granules, pellets, or other form) within the filter member 24. Preferably, if the filter medium is provided in loose form, there is (but need not be) some type of containment component that prevents the filter medium from leaking or falling out of the filter member 24. The filter medium can be provided either on a supporting component, in a supporting component, or both on and in a supporting component. In one non-limiting example, the supporting component could be a pervious material, such as a pervious piece of foam. The filter medium could be provided in the form of particles, or some other form, that is disposed on or within the piece of foam, or other pervious material. Alternatively, or additionally, the filter medium could be integrally formed with such a supporting material. One non-limiting example of this would be for baking soda to be included in the composition that is used to form a pervious foam material. The filter medium can be provided in one or more containers that comprise the filter element 40. These container(s) can comprise boxes, bags (such as tea bag-type elements), sachets, or other containers. These containers may be made of a porous material, or may have holes or apertures therein to facilitate air flow. The filter media may be provided in and/or on flat or corrugated or textured filter elements (which may resemble, but are not required to resemble, furnace filters (permanent or disposable)). These containers or filter elements, if there is more than one of each, can be arranged in any suitable relationship to each other, including, but not limited to: stacked, and side-by-side, with or without space therebetween. The examples of types of filter elements described above can also be combined in any manner to produce yet other filter elements.

Figure 6:
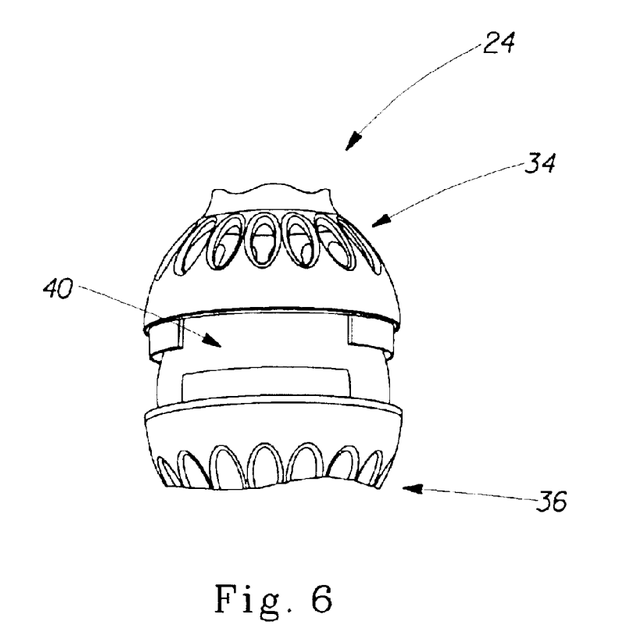
FIG. 6 is a side view of the cartridge shown in the preceding figures which is partially opened to show the filter medium.
Figure 7:
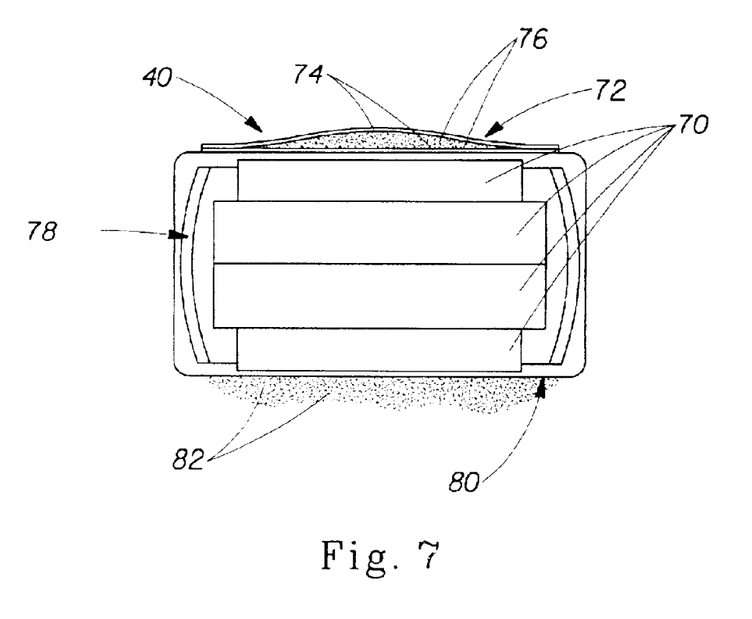
FIG. 7 is a schematic cross-section of the filter medium shown in FIG. 6.

FIG. 7 is a schematic cross-section of one non-limiting example of a filter element (or "filter") 40 suitable for use in the embodiment of the filter member 24 shown in FIGS. 3, 4, and 6. The filter element 40 shown in FIG. 7 combines several of the types of filter elements described above. (It should be understood, however, that this is primarily for the purposes of illustration of the various different types of filter elements, and it is not necessary that a filter element comprise all of these components.)

The filter element 40 shown in FIG. 7 comprises several disks 70 which can have the filter media (such as activated carbon, baking soda, or both) thereon and/or therein. The disks 70 can be made of any material suitable for this purpose. If it is desired to allow air to flow through the filter element 40, the disks should be pervious to air flow. In the embodiment shown, the disks 70 are comprised of a porous foam that is pervious to air flow. The disks 70 are placed atop one another. Additional filter media, such as baking soda, activated carbon, or both, can be placed on top of the stack of disks 70, below the stack of disks, or on the sides of the stack of disks (e.g., wrapped around the stack of disks). These filter media can be arranged in a virtually unlimited number of combinations of different manners (e.g., different spatial relationships and different types of filter media).

For example, in one non-limiting embodiment, a container, such as a sachet or small pervious bag of baking soda 72 can be placed on top of the disks 70. The sachet 72 shown in FIG. 7 comprises a pair of porous side walls 74 having baking soda 76 therebetween. The baking soda 76 can be in any suitable form, including, but not limited to powder or granules. The container 72 can have the baking soda disposed therein in sufficient thickness that air is unable to flow through the container 72 as a result of action of the fan, and the baking soda 76 can only serve to deodorize air that moves past the container 72. Preferably, however, the container of baking soda 72 has the baking soda disposed therein (whether it be by distributing the baking soda in a sufficiently thin layer, by placing portions of the baking soda into separate compartments, or by some other mechanism) such that air pulled in by the fan will flow through the container of baking soda 72 without an excessive drop in pressure (or air flow rate).

The disks 70 can have activated carbon and/or baking soda affixed thereto. Around the stack of disks 70 is wrapped a first wrapping (or if there is no other wrapping, "the wrapping"), such as a piece of nonwoven material 78. The first wrapping 78 can have any suitable filter media thereon. In one non-limiting example, the first wrapping 78 can have baking soda on the inside portion thereof. In another non-limiting example, the first wrapping 78 can have potassium permanganate thereon for ethylene removal. To prevent spillage of any filter media particles, this entire assembly may be contained in a second wrapping, such as a piece of woven nylon 80. In one embodiment, the nylon is stretched to a point such that the average pore size of the woven piece of nylon is less than about 0.5 mm$^2$. In another non-limiting example, a larger sachet with baking soda therein could be wrapped around the stack of disks 70. This larger sachet can be used as a replacement for the first and/or second wrappings, or in addition to the first and/or second wrappings.

Additional filter media can also be located below this assembly. For example, in one non-limiting embodiment, media such as in the form of granules 82, or another sachet can be provided underneath the filter to provide additional odor removal capacity. In other non-limiting embodiments, instead of comprising a stack of disks, the filter element could comprise arrangements of one or more containers (including, but not limited to a stack or row of containers, with or without space therebetween) containing filter media. Numerous other embodiments are possible. It should also be understood that the filter element 40 of the present invention need not comprise all the elements described herein (which are shown merely to illustrate some of the possible variations), but may instead comprise only one, or more, of these elements.

Confined spaces often have complex structures so that normal air convection does not reach every corner of the confined space. Such complex structures for example include separate compartments such as drawers or hollow elements inside the confined space. Therefore, it is often insufficient to deodorize such confined spaces with only a single device, even a forced air device having a fan.

In accordance with one aspect of the method of the present invention, it is possible to also deodorize those portions of the confined space which are not sufficiently accessible to normal air convection. This is achieved by utilizing more than one filter member. Each of those filter members can be positioned independently of each other and used as passive filters. One of the filter members optionally may be used while connected to an air moving member.

A confined space for which one aspect of the method of the present invention is particularly suitable comprises a compartment (e.g., the vegetable drawer in a refrigerator) which is within a confined space (the refrigerator) but which is separated from the remainder of the confined space (the interior of the refrigerator). In this case, one of the filter members may be placed in the separate compartment and another filter element may be placed in the remainder of the confined space. With the method of the present invention it is therefore possible to deodorize all compartments in a confined space such as a refrigerator (which has enclosed compartments for vegetables, meats, etc.), a closet (which has shoe storage closets, clothes storage containers, etc.), or the like. In particular when the separate compartments differ in size, it may be beneficial to place a forced air filter member in the larger compartment and a passive filter member in the smaller compartment.

A forced air device will enable removal of more malodors to happen more quickly than a passive device by increasing the rate of air contact with the adsorbing media. As such, a forced air device as described above is suitable for use in the large area of a confined space (e.g. the interior of a refrigerator, a closet, etc.) as it has the ability to move the relatively large volume of air in these spaces, typically 50 to 800 liters, through or past the filter media. A passive device is suitable for use in the smaller compartments within a confined space (vegetable drawers, shoe storage containers, etc.) where diffusion alone is effective at moving air to the filter media, and where the air is not accessible to the forced air device.

When the apparatus of the present invention is used as a deodorizing device, it is used by inserting a battery in the air moving member 22 (if one is not already therein), and placing the air moving member 22 along with a cartridge member 24 in a confined space to be deodorized. The cartridge member 24 may be placed directly on top of the air moving device 22, and will remain held in place thereon by gravitational forces and the surface topology of the interfacing parts of the cartridge member and the air moving member. For instance, as shown in the drawings, the interfacing parts of the cartridge member 24 and the air moving member 22 may match each other such as if each has a complementary hemispherical design. The forced air filter apparatus 20 is preferably placed in one of the larger confined spaces to be deodorized, such as in the interior of a refrigerator.

A second (and third, fourth, etc.) cartridge member 24 may be placed in one of the smaller confined spaces to be deodorized, such as in one or more of the drawers of the refrigerator, and used as a passive filter. Alternatively, one or more of the cartridge members 24 could be placed in one of the larger confined spaces to be deodorized and used as a passive filter, and the entire apparatus could be placed in the larger confined space to be deodorized. In addition, the cartridge members can be placed in other confined spaces to be deodorized, which other spaces are independent of the location in which the apparatus is placed. For example, the apparatus could be placed in a refrigerator, and the additional cartridge members could be placed in dresser drawers, or any other confined spaces.

When the cartridge member 24 is exhausted, the cartridge member 24 can simply be lifted off the air moving member 22, and replaced with a fresh cartridge 24. The cartridge members 24 in the other confined spaces can similarly be replaced with fresh cartridges when they are exhausted.

When used for deodorizing, the apparatus can provide several benefits, especially in confined spaces such as refrigerators, including, but not limited to: removing malodor from confined spaces; removing ethylene from confined spaces; maintaining the fresh odor of confined spaces; reducing the transfer of airborne bacteria in confined spaces; maintaining the freshness of food items; improving the quality of food items; maintaining the fresh taste of food items; preventing the transfer of odors between two food items; extending the useful life of food items; keeping food items fresh over a longer period of time; reducing spoilage of food items; reducing the incidence of freezer burn of food items in a freezer compartment; maintaining the fresh taste and/or odor of ice cubes (preferably ice cubes made by an automatic ice maker); increasing the cooling efficiency of a refrigerator; preventing or reducing the formation of ice crystals on ice cream in an opened or partially-sealed box stored in a freezer compartment; and combinations thereof. The present invention further relates to the use of the apparatus to achieve such benefits (i.e. technical effects).

The apparatus can be provided in the form of a package or kit which comprises: (a) an apparatus selected from the group consisting of one or more passive filter members, a forced air filter member, and combinations thereof; (b)

optionally, a package containing the apparatus; and (c) optionally informational indicia, including printed matter such as a set of instructions, in association with the apparatus or the package to communicate the method of using the apparatus and/or benefits thereof to a consumer.

The apparatus is optionally, but preferably contained in a package that protects the apparatus during shipment and/or makes the apparatus easier to display in a retail store or more appealing to consumers. The optional package can comprise any suitable type of package, including but not limited to: cardboard boxes, bubble-wrap films, thermo-form plastic packaging, expanded cellular polystyrene (e.g. STYROFOAM™), and the like.

The apparatus may also be provided with optional informational indicia which communicates the benefits (i.e. technical effects) of the apparatus to consumers. Without the informational indicia, consumers who otherwise might not use the apparatus (e.g. because they were not aware of the potential benefits/technical effects derived from using the apparatus), will use the apparatus to obtain the benefits, such as preserving the quality of food, and the like.

Informational indicia can be provided in association with the apparatus itself or, when the apparatus is contained in a package, in association with the package. As used in this context, the phrase "in association with" means the informational indicia (e.g., a set of instructions) are either directly printed on the apparatus itself (or package itself) or presented in a different manner including, but not limited to, a video tape, a brochure, print advertisement, electronic advertisement, and/or verbal communication, so as to communicate the set of instructions to a consumer of the apparatus. Informational indicia can include, but is not limited to: a set of instructions that direct a consumer how the steps need to be carried out (such as the methods of use described herein) to obtain the communicated benefits; diagrams, pictures, and/or logos which communicate the benefits and steps which need to be carried out to obtain the benefits; and the like.

Numerous other embodiments of the apparatus and method of the present invention, as well as other features for the same, are possible. A couple of non-limiting examples are described below.

Figure 8:
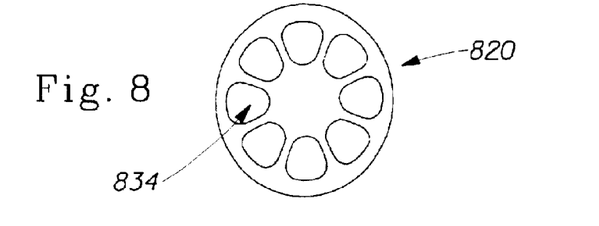
FIG. 8 is a top view of an alternative embodiment of the device of the present invention.
Figure 9:
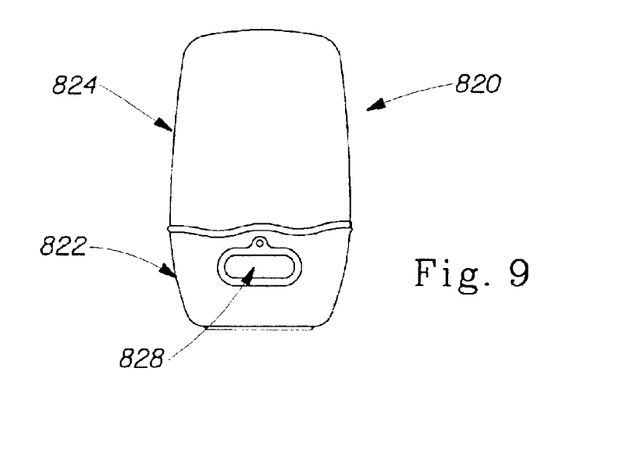
FIG. 9 is a side view of the device shown in FIG. 8.

FIGS. 8 and 9 show an alternative embodiment of the device of the present invention. In FIGS. 8 and 9, a device 820 is provided which comprises at least one air inlet 834, air outlets 828 on each side of the base 822 and a removable and replaceable filter member 824. The filter member 824 is placed onto the base 822 such that air flow from a fan draws air through the top of the filter member 824 and through the air outlets 828 on the base 822.

In this example, the filter member 824 contains a filter element and a battery. The filter element is designed to exhibit the same useful lifetime as that of battery so that both may be replaced as a single unit. The filter member 824 contains two metal contacts allowing an electrical current to flow from the battery to the base 822. The filter element of the device can be any of the types of filter elements described for the embodiment shown in FIG. 1. The filter element can be shaped such that a battery, such as a 1.5 volt dry alkaline "D" battery, fits inside a void in the filter element.

Similar to the embodiment shown in FIG. 1, the base 822 contains a fan, motor and a circuit board which controls the motor and an LED (not shown) which blinks to indicate the upcoming need to replace the filter member 824 containing the battery and filter medium. Further, the base 822 also contains metal contacts allowing current to flow from the battery (contained in the filter assembly) to the motor.

Figure 10:
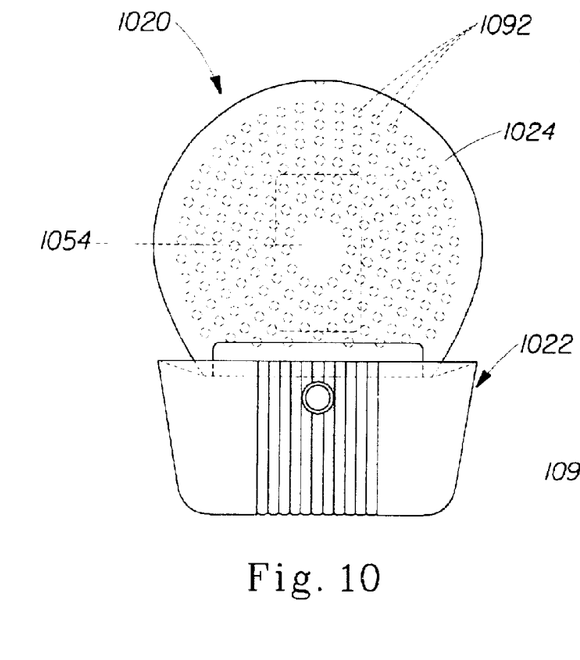
FIG. 10 is a side view of another alternative embodiment of the device of the present invention.
Figure 11:
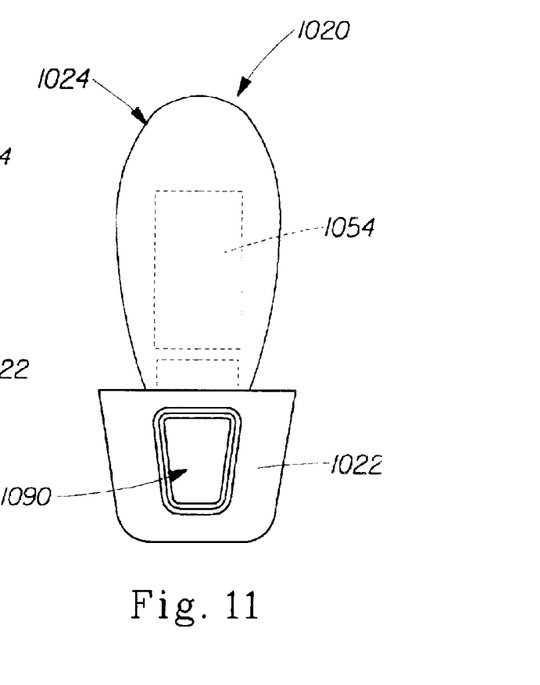
FIG. 11 is an end view of the device shown in FIG. 10.

FIGS. 10 and 11 show another alternative embodiment of the device of the present invention. In FIGS. 10 and 11, a device 1020 is provided which comprises an air inlet 1090 on each side of the base 1022, multiple air outlets 1092, and a removable and replaceable filter element member 1024. The filter member 1024 is placed onto the base 1022 such that air flow from a fan draws air through the air inlets 1090 in the base 1022, through the filter medium inside the filter member 1024, and out through the air outlets 1092 in the filter member 1024.

In this example, the filter member 1024 also contains a filter element and a battery. The filter element is designed to exhibit the same useful lifetime as that of battery so that both may be replaced as a single unit. The filter member 1024 contains two metal contacts (not shown) allowing an electrical current to flow from the battery 1054 to the base 1022. The filter element of the device can be any of the types of filter elements described in the example of FIG. 1. The filter element is shaped such that air is forced from the base 1022 into the bottom and middle of the filter element and then must travel through the filter element to flow outward through the air outlets 1092. Further, this filter element is shaped such that a 1.5 volt dry alkaline "D" battery fits inside a void in the filter element.

In this example, the base 1022 may contain multiple fans and motors to provide more air flow through the filter assembly. Because of the filter housing geometry, the best performance with this device is obtained by using two centrifugal fans, powered by one or two motors. The base contains a circuit board which controls the motors and an LED (not shown) which blinks to indicate the need to replace the filter member 1024 containing the battery 1054 and filter medium. Further, the base 1022 may also contain metal contacts allowing current to flow from the battery 1054 (contained in the filter assembly) to the motors. Optionally, the base 1022 may be designed to contain the replaceable battery, eliminating the battery from the filter member 1024.

The apparatus and method of the present invention may also be used for emitting a scent, or other substance (including, but not limited to insecticides, air fresheners, deodorants, aromacology, aromatherapy, or any other substance or odor that acts to condition, modify, or otherwise charge the atmosphere or to modify the environment) into the air. It should be understood that the following will describe the emitting apparatus in terms of scent-emissions for simplicity. The apparatus and method described herein can apply to the emission of all the other types of substances described herein. It is possible to use the device for emitting a scent into the air either with, or without including the technology described herein to remove malodors from the air. In order to convert the apparatus to an emitting device, the filter element can be replaced with scent-containing media, or alternatively, scent-containing media can be added to any of the filter elements described herein.

The scent-containing media can be in any suitable form including, but not limited to: perfume oils, liquid distributed via a wick, scented gels, scented beads, scented cellulose, scented activated carbon, or other scent-containing media. If the scent-containing media is in the form of a scented gel, the scented gel can be made from a neat perfume oil combined with a thickening agent. Suitable thickening agents include starches such as hydroxypropyl cellulose, or fumed silica. Any suitable proportions of these components can be used.

The scent-containing media can be provided in any suitable structure or arrangement. The scent-containing media, as noted above, may be placed in an emitting member similar to the cartridge member 24 for the deodorizing device described above. The air moving member 22 can be identical to that used in the air deodorizing device. In other embodiments, the air moving member 22 may only be similar to that used in the air deodorizing device. In still other embodiments, the air moving member 22 may be a completely different type of device.

In certain embodiments, it may be desirable to maximize the surface area to volume ratio of the scent-containing media. There are numerous ways to maximize the surface area to volume ratio of the scent-containing media. These include, but are not limited to providing the scent media on corrugated or honeycomb type structures. It is also desirable to obtain maximum contact of the air with the scent-containing medium. In some embodiments, therefore, it is desirable for the surface area of the scent-emitting medium to be greater than or equal to about five times, or more preferably greater than or equal to about ten times the cross-sectional area of the air flow path (the latter being measured in a direction perpendicular to the direction of air flow). If the cross-sectional area of the air flow path varies in size from the air inlet to the air outlet, the maximum cross-sectional are of the air flow path is used.

If the scent-containing media is provided in the form of a gel, it is preferable that the gel be oriented so that the air flow is not blocked as it flows through or around the gel. There are a non-limiting number of types of arrangements so the gel does not block the air flow. In one embodiment shown in FIG. 12, the mass of scented gel 100 has an interior that is formed into a hollow cylinder 102. The hollow cylinder 102 has an axis, A, that is preferably oriented in substantially the same direction as the air flow (shown by the arrows). The mass of scented gel 100 can be provided in a cartridge, having an outer shell represented schematically as reference numeral 120. This cartridge can have an air inlet 122 and an air outlet 124. The mass of scented gel can be continuous (as opposed to a plurality of gel beads), or it can be comprised of one or more pieces of gel that fit together.

Figures 12, 13, 14:
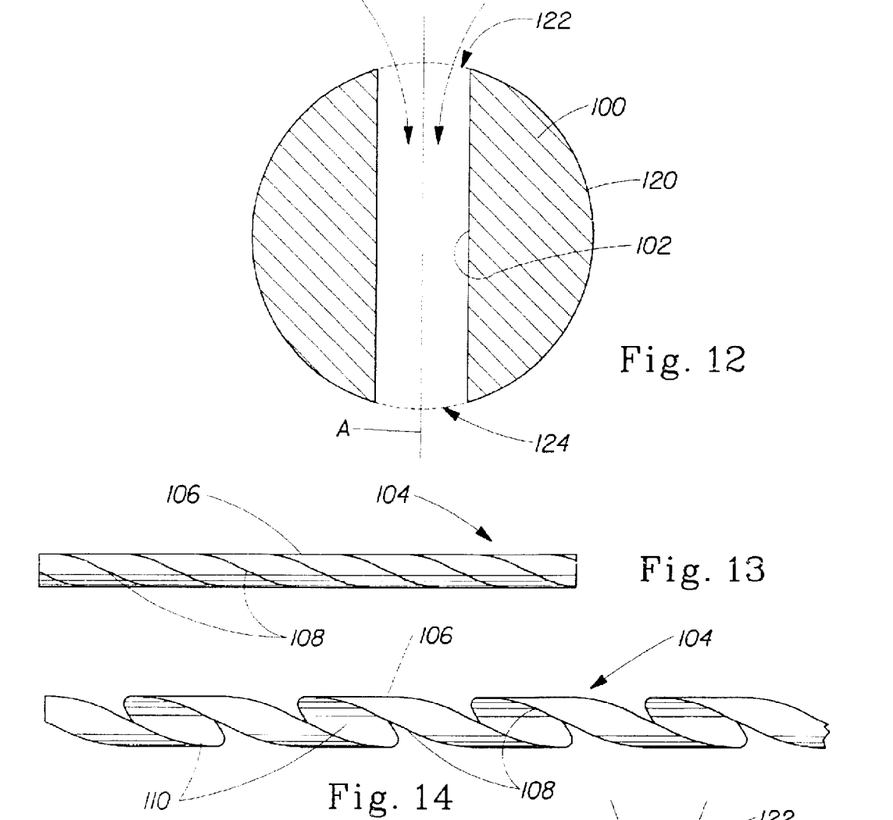
FIG. 12 is a schematic cross-sectional view of a portion of a cartridge for an embodiment of the device used for emitting scents in which the scent-emitting media is in the form of a hollow cylinder.
FIG. 13 is a schematic side view of an embodiment in which the scent emitting media is inside a spirally-wound tube, shown prior to twisting the tube.
FIG. 14 is a schematic side view of the spirally-wound tube shown in FIG. 13 in which the tube has been twisted to expose the scent-emitting media through gaps therein.

FIGS. 13–16 show other embodiments in which the scent-containing media is located in tube-shaped structures. FIG. 13 shows a scent-containing structure 104 that resembles a spirally-wound or spirally-cut soda straw. The scent-containing media, such as a scented gel, is placed on the inside surface of the wrapper 106 that forms the soda straw structure. The wrapper 106 comprises at least one rupturable zone, which in this embodiment is in the form of spiral cuts or weakened areas 108. FIG. 13 shows this structure prior to any mechanical manipulation of the same, when the spiral cuts or weakened areas 108 are closed and the scented gel therein is not exposed to the environment. FIG. 14 shows the structure shown in FIG. 13 after the same has been twisted or stretched so that the structure separates at the spiral cuts or weakened areas 108 for the purpose of exposing the scent-containing media 110 to the environment.

Figure 15:
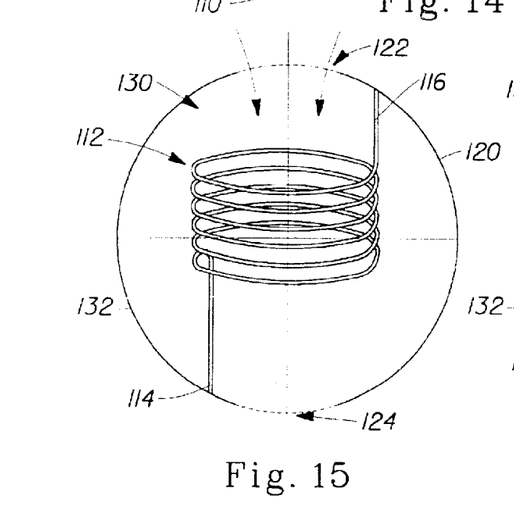
FIG. 15 is a schematic side view of a coiled tube structure containing scent-emitting media, shown with the coils tightly coiled to reduce the amount of scent-emitting media that is exposed.
Figure 16:
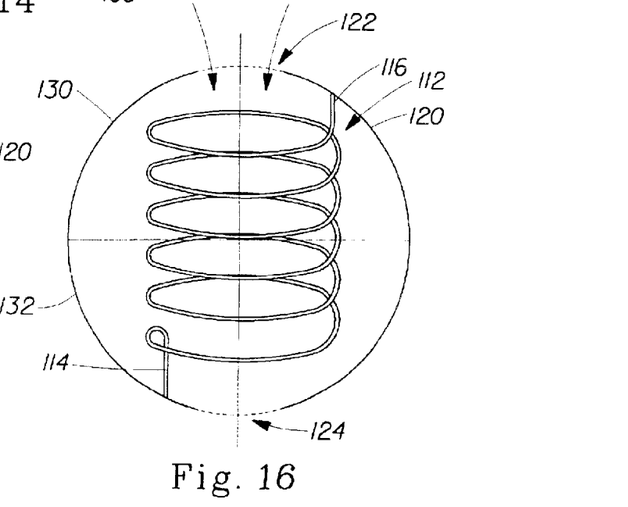
FIG. 16 is a schematic side view of a coiled tube structure containing scent-emitting media, shown with the coils expanded to increase the amount of scent-emitting media that is exposed.

FIG. 15 shows a scent-containing structure 112 that is formed into a spiral or helical coil. The overall spiral or helically-coiled structure 112 is in the form of a tube. The scent-containing structure shown in FIG. 15 can be formed of a longer length of the type of structure shown in FIGS. 13 and 14. The scent-containing structure shown in FIG. 15 is placed in a cartridge similar to the cartridge member 24 for the deodorizing device described above. The cartridge has an outer shell 120 having a top portion 130 and a bottom portion 132. The tube formed by the helically-coiled structure 112 is also preferably oriented with its axis, A, in substantially the same direction as the air flow. The helically-coiled structure 112 has two ends 114 and 116. Such an embodiment can be provided with the ends 114 and 116 of the helically-coiled structure 112 affixed on the inside surface of the outer shell 120 of the cartridge. The ends 114 and 116 of the structure 112 are affixed to opposite portions of the outer shell 120 of the cartridge (e.g., 130 and 132). This enables a user to increase the intensity of the scent by turning one portion of the cartridge (e.g., 130) relative to the other (e.g., 132) as shown in FIG. 16, and thus increase the exposed surface area of the gel.

The device described herein can be used for emitting a scent or substance in any of the manners specified herein for use in removing malodors from the air. For example, a first emitting member can be used for emitting a substance with the air moving member, and a second emitting member can be used independently of the first emitting member and air moving member to passively emit the same or different substance into the air. The device can be provided to consumers in the form of a kit which contains air deodorizing media, substance emitting media, or both. Consumers can also use these various types of cartridges interchangeably with the air moving member or separately from the air moving member.

When the device is used for emitting substances, it will operate in the same manner as described above when it is used for deodorizing confined spaces. Thus, for example, a cartridge 24 with emitting media contained therein can be placed on top of the air moving member 22, and air will be drawn into the cartridge past or through the emitting media, and will be emitted through the air outlets 28 of the air moving member. When the device is used for emitting substances, it is possible to effectively use the device for emitting substances in even larger confined spaces, such as in a room, or a closet.

In still other embodiments, the device can be used to both deodorize and emit a substance into the air, such as a scent to fragrance or freshen the air. Developing such a device presents challenges because the various types of odor removing media are generally not capable of selectively removing malodors from the air. As a result, there will be a tendency for the device to remove perfume molecules as they are emitted, defeating the dual purpose of the device.

Figure 17:
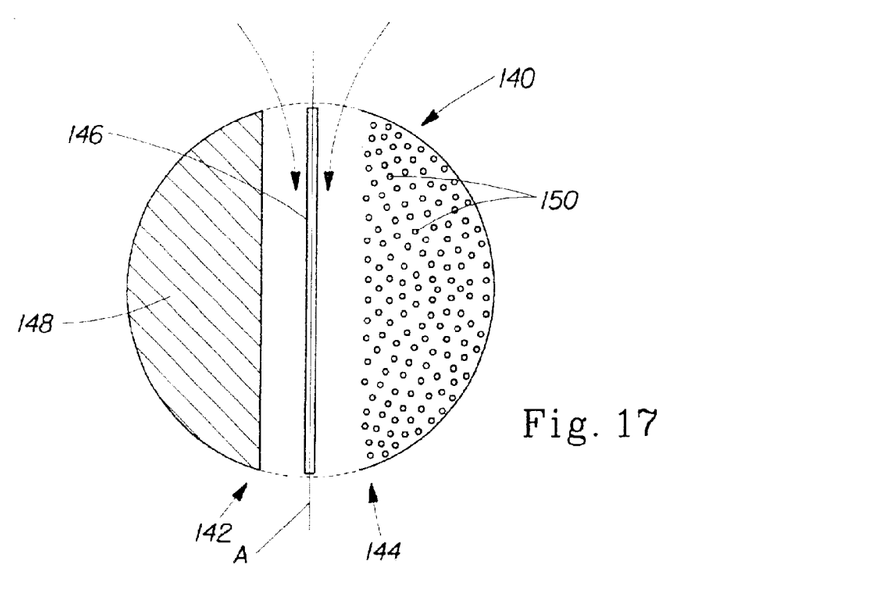
FIG. 17 is a schematic cross-sectional view of a portion of a cartridge that is capable of both deodorizing and emitting a material.

One way of dealing with this undesired tendency is to separate the odor removing time periods and the scent emitting time periods. In one non-limiting embodiment shown in FIG. 17, the device can include a removable cartridge member 140 similar to the filter member 24 of the air deodorizing device. This cartridge member 140 is modified so that it is split longitudinally into two halves 142 and 144 along the axis, A, of airflow. The two halves 142 and 144 of the cartridge member 140 are separated by an impermeable wall 146. One half 142 of the member 140 is filled with a scent emitting media, such as a perfume gel 148. The other half 144 of the member 140 is then filled with an odor adsorbing medium 150, such as activated carbon or zeolite. This could be pelletized, powdered, or most preferably supported on an open foam. The design of the air inlets on the device is preferably such that the fan unit is either moving air through the filter media or the scent media, but not both. The setting of the unit can be changed from its odor removal function to its scent emitting function by manually rotating the filter member from one position to the other. Alternatively, the change from odor removal to scent-emitting function can be accomplished by automatic rotation of the filter member. This rotation can be controlled by an electrical timer or a non-electrical means, such as a spring.

The devices described herein can be provided with a non-limiting number of optional features. Some of these optional features may be more desirable when the device is used for emitting substances, although these features can also be used in the context of a deodorizing device.

For example, the air moving member, the passive member, or both, may be provided with an intensity control (or an "intensity controlling mechanism"). The intensity of the substance emitted from the device can be controlled by any suitable type of intensity controlling mechanism.

Figures 18, 19:
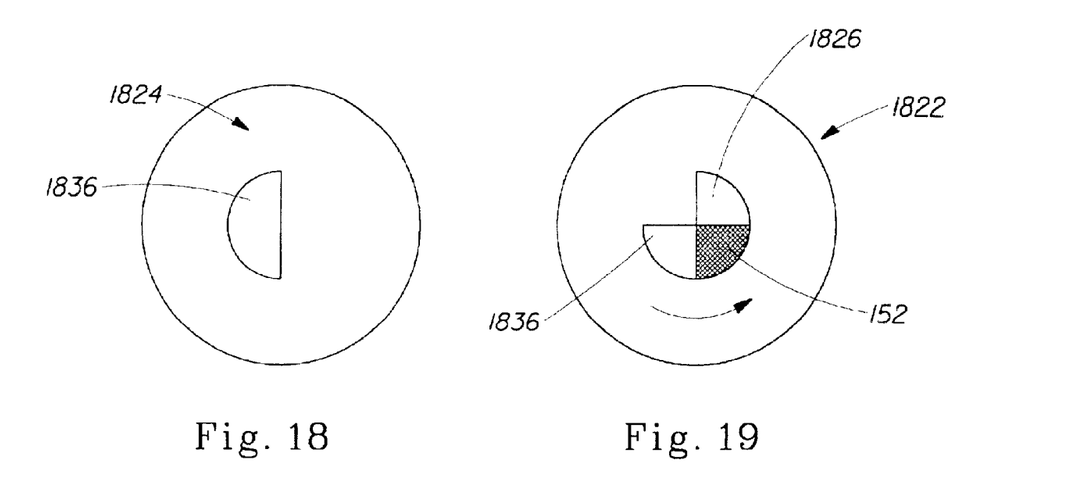
FIG. 18 is a schematic view of one embodiment of a mechanism for controlling the intensity of the scent (the mechanism shown can represent the bottom of the scent cartridge or top of the air moving member, either of which can be provided with a configuration that is capable of at least partially blocking the flow of air therethrough).
FIG. 19 is a schematic top view of the interface between the bottom of the scent cartridge and the top of the air moving member showing how the two interact when provided with the mechanism shown in FIG. 18 to reduce the amount of airflow and scent intensity.

In certain embodiments, the intensity controlling mechanism comprises a mechanism for adjusting the air flow through the device. The air flow path can, for example, be partially or fully opened and closed. One non-limiting version of such a mechanism is shown in FIGS. 18 and 19. FIG. 18 is a schematic view of one embodiment of a mechanism for controlling the intensity of the scent. The component shown in FIG. 18 can represent the bottom of a scent cartridge 1824 or top of the air moving member 1822 of a scent emitting device similar to the embodiment shown in FIG. 1, either of which components can be provided with a configuration that is capable of at least partially blocking the flow of air therethrough. (It should also be understood that this feature can be provided on any other embodiment contemplated herein). For simplicity of description, the element shown in FIG. 18 will be designated as representing the bottom of the scent cartridge 1824. As shown in FIG. 18, the bottom of the scent cartridge 1824 has an air outlet 1836 that is in the shape of a semi-circle. It should be understood that the air inlets and air outlets are not limited to semi-circular shapes, but can be provided in any suitable configuration.

FIG. 19 is a schematic top view of the interface between the bottom of the scent cartridge 1824 and the top of the air moving member 1822 showing how the two interact when provided with the mechanism shown in FIG. 18 to reduce the amount of airflow and scent intensity. Turning the cartridge relative to the openings of the air moving member 1822 will change the size of the opening of the air flow path (open or close the same), thus changing the total air flow and intensity of the substance emitted. In the embodiment shown in FIG. 19, the cartridge 1824 has been turned 90 degrees counter-clockwise relative to the air moving member 1822. This covers half of the total area of the air inlet 1826 of the air moving member 1822, leaving the area 152 unobstructed, and reducing the amount of air flowing through the device.

In an alternative embodiment, rather than blocking the air flow, the intensity controlling mechanism can comprise a component that covers a portion of the surface area of the scent emitting media. Such a component can be in the nature of a shutter-type component.

Figure 20:
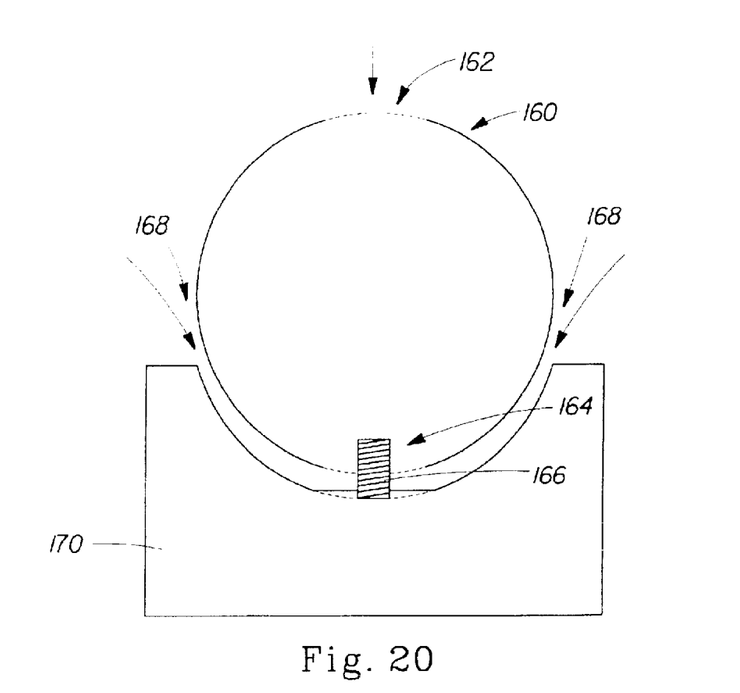
FIG. 20 is a schematic cross-sectional view of a scent-emitting device having a screw-like mechanism for intensity control shown with the intensity control set for a low intensity setting.
Figure 21:
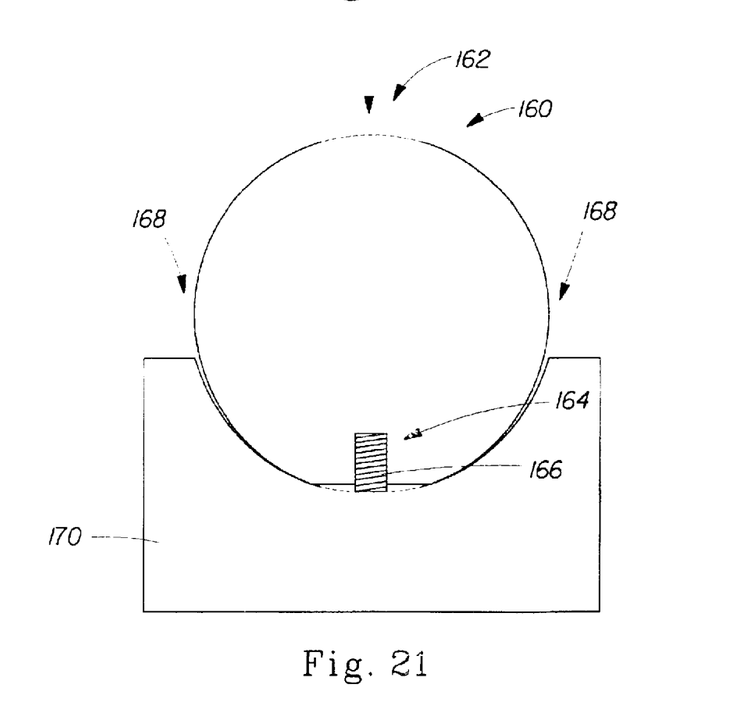
FIG. 21 is a schematic cross-sectional view of the scent-emitting device shown in FIG. 20 in which the intensity control is set for a high intensity setting.

In other embodiments, the intensity is adjusted by altering the amount of air that flows past the emitting media. In one non-limiting category of such an embodiment, the intensity controlling mechanism comprises a mechanism for moving the scent emitting member apart from the air moving device. A version of this embodiment is shown in FIGS. 20 and 21. The embodiment shown in FIGS. 20 and 21 comprises a scent cartridge 160, having an air inlet 162 and an air outlet 164. In the embodiment shown in FIGS. 20 and 21, the mechanism comprises a screw element 166 that can raise and lower the cartridge 160 when the cartridge 160 is rotated. The intensity controlling mechanism is not limited to screw elements. Any type of device known that can move the scent cartridge 160 apart from the air moving device 170 can be used. When the cartridge 160 is raised, this will create alternate air inlets or passages 168 for the air moving device. This will reduce the amount of air which is passed through the scent cartridge 160. The advantage of this embodiment is that the total airflow through the air moving member 170 remains the same. This will provide consistency in the distribution of the scent throughout a room, rather than having the scent distributed to a smaller area when the intensity setting is lowered.

In addition to the foregoing, an article can be provided for storing one or more emitting members so they can be re-used, and/or used interchangeably. In one nonlimiting embodiment, the article can comprise a storage case. Such a storage case can be provided with a number of features including, but not limited to, separate sealed compartments so that the substances in the emitting members will not co-mingle.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A system for deodorizing air and/or emitting one or more substances into the air comprising:

a first deodorizing and/or emitting device comprising an air moving member and a first passive deodorizing and/or emitting member configured for use with said air moving member, said first passive deodorizing and/or emitting member being detachable from said air moving member and being capable of being used independently from said air moving member, said first passive deodorizing and/or emitting member comprising a first medium, at least a portion of which comprises a first substance that serves to deodorize the air and/or is to be emitted into the air;

one or more additional deodorizing and/or emitting members comprising passive deodorizing and/or emitting members, said one or more additional deodorizing and/or emitting members being detachable from said air moving member and being capable of being used independently from said air moving member comprising a medium, at least a portion of which comprises a second substance that serves to deodorize the air and/or is to be emitted into the air, wherein said one or more additional deodorizing and/or emitting members can be used with said air moving mumber, and at least one of said first substance and said second substance comprises a deodorizing substance that removes malodor molecules from the air.

2. The system of claim 1 wherein said first and second substances are the same.

3. The system of claim 1 wherein said first and second substances comprise deodorizing substances comprising a first deodorizing substance and a second deodorizing substance, and said first and second deodorizing substances are different.

4. The system of claim 1 wherein said first deodorizing and/or emitting device is battery powered.

* * * * *